ion of a herbicidal bipyridylium diquaternary salt with

United States Patent [19]

Tadros

[11] Patent Number: 4,875,927
[45] Date of Patent: Oct. 24, 1989

[54] FORMULATION PROCESS

[75] Inventor: Tharwat F. Tadros, Wokingham, England

[73] Assignee: Imperial Chemical Industries PLC, London, England

[21] Appl. No.: 143,348

[22] Filed: Jan. 13, 1988

[30] Foreign Application Priority Data

Jan. 13, 1987 [GB] United Kingdom ............... 8700658

[51] Int. Cl.$^4$ ........................................... H01N 25/32
[52] U.S. Cl. .......................................... 71/94; 71/92; 71/DIG. 1
[58] Field of Search ..................... 71/94, 92, DIG. 1

[56] References Cited

U.S. PATENT DOCUMENTS

| | | | |
|---|---|---|---|
| 3,479,176 | 11/1969 | Wilson | 71/DIG. 1 |
| 4,075,005 | 2/1978 | Knowles et al. | 71/DIG. 1 |
| 4,115,098 | 9/1978 | Stull | 71/92 |
| 4,244,816 | 1/1981 | Vogler et al. | 210/638 |
| 4,385,049 | 5/1983 | Cuca | 424/167 |
| 4,446,051 | 5/1984 | Berthod et al. | 252/309 |

FOREIGN PATENT DOCUMENTS

| | | |
|---|---|---|
| 1045976 | 9/1979 | Canada . |
| 0006293 | 1/1980 | European Pat. Off. . |
| 1128848 | 10/1968 | United Kingdom . |
| 2002400 | 2/1979 | United Kingdom . |
| 2156799 | 10/1985 | United Kingdom . |

OTHER PUBLICATIONS

Journal of Controlled Release, 3, (1986), May, No. 4, Amsterdam, Netherlands "Stabilisation of W/O/W Multiple Emulsions by Interfacial Complexation . . . ".
Asher et al., "Liquid Membrane Capsule System for the Treatment of Chronic Uremia", May 10, 1974.

Primary Examiner—Catherine L. Mills
Attorney, Agent, or Firm—Cushman, Darby & Cushman

[57] ABSTRACT

A process of preparing a herbicidal emulsion comprising 75 grams per liter or more of a salt of a herbicidal bipyridylium diquaternary cation as an active ingredient comprising as a first step agitating an aqueous solution of a herbicidal bipyridylium diquaternary salt with an oil and a first emulsifier having a low HLB value to give a first emulsion comprising droplets of herbicidal bipyridylium diquaternary salt solution dispersed in a continuous oil phase, and as a second step, agitating the first emulsion with water and a second emulsifier having a high HLB value, to give a second emulsion comprising drops of the first emulsion dispersed in a continuous aqueous phase. The emulsions have a lower oral toxicity than conventional aqueous formulations.

7 Claims, No Drawings

FORMULATION PROCESS

This invention relates to methods of preparing herbicidal compositions comprising a multiple emulsion containing a bipyridylium diquaternary salt as the active ingredient.

Various herbicidal bipyridylium diquaternary salts are described in U.K. Patent Specification Nos. 785732, 813531 and 813532. Certain of these compounds are in widespread use in agriculture, and are manufactured for sale in the form of concentrated aqueous solutions. When required for use, these concentrated solutions are diluted with water to form a solution which is then sprayed upon unwanted plants. When used with due care, and in accordance with recommended procedures, the concentrated aqueous solutions present no hazard. However, hazards may develop if adherence to the recommended handling practices is not maintained. Thus it may happen that an operator may decant some of the concentrate into a domestic container such as a beverage bottle for subsequent use in his own garden at home. The hazard associated with such a practice is of course that a child or incautious adult coming upon the bottle may swallow some of the contents, with possible serious consequences.

Various methods have been proposed to reduce the likelihood of accidental swallowing of concentrated solutions of bipyridylium diquaternary salts in the circumstances described above. These include the inclusion of an odourant in the concentrate as a warning (see U.K. Pat. Nos. 1406881 and 1570981) and the addition of a gelling agent (see U.K. Pat. No. 1395502). Another approach has been to include an emetic in the concentrate, so that the concentrate will be regurgitated shortly after its ingestion (See U.K. Pat. No. 1507407). In addition to methods of formulating bipyridylium herbicides so as to reduce the likelihood of accidental ingestion, a variety of methods has been proposed for formulating bipyridylium herbicides so as to improve their suitability for particular applications. Thus, it has been proposed to formulate an aqueous solution of paraquat as an invert emulsion in oil (see U.S. Pat. No. 4,115,098) in order to reduce drift and evaporation of the droplets of spray when the paraquat is applied as a herbicide.

A method of formulating herbicidal bipyridyllium diquaternary salts as a multiple emulsion has now been devised, whereby the concentrated aqueous solution of the herbicidal bipyridylium diquaternary salt is emulsified in an oil by agitation with a suitable emulsifier, to give an emulsion (the "first emulsion") wherein droplets of the aqueous solution are dispersed through a continuous oil phase. The first emulsion is then itself dispersed by agitation into an aqueous solution containing a second emulsifier to give a multiple emulsion (the "second emulsion") which comprises drops of the first emulsion dispersed in a continuous aqueous phase. The drops of the first emulsion themselves contain droplets of the concentrated aqueous solution of the herbicidal bipyridylium salt. The oil surrounding these droplets of aqueous bipyridylium salt solution acts as a barrier and prevents the bipyridylium salt from passing out into the continuous aqueous phase. Preferably, the continuous aqueous phase contains a solute to maintain osmotic balance between this phase and the aqueous solution of bipyridylium salt. When required for use as a herbicide, the multiple emulsion is diluted and agitated with water. The emulsion then either breaks up and liberates the herbicidal bipyridylium diquaternary salt into the aqueous spray solution or when the spray solution is applied to weeds the emulsion breaks up or evaporates on the surface of the weeds to liberate the bipyridylium herbicide. However, if a quantity of the concentrated multiple emulsion formulation is inadvertently swallowed, as a result for example of transfer of the concentrate to a beverage bottle as mentioned above, the volume of fluid in the gastrointestinal tract and the osmotic differential between this fluid and the solution of the herbidical bipyridylium diquaternary salt are insufficient in combination to break down the multiple emulsion to any substantial extent. The bipyridylium diquaternary salt accordingly remains substantially contained in the drops of the emulsion, which passes along the gastro-intestinal tract with a substantial reduction in the amount of the bipyridylium diquaternary salt absorbed through the gut wall or into the bloodstream as compared with the absorption which takes place as a result of swallowing an aqueous solution of a bipyridylium diquaternary salt.

According to the present invention therefore, there is providing a process of preparing a herbicidal emulsion comprising 75 grams per liter or more of a salt of a herbicidal bipyridylium diquaternary cation as an active ingredient comprising as a first step agitating an aqueous solution of a herbicidal bipyridylium diquaternary salt with an oil and a first emulsifier having a low HLB value to give a first emulsion comprising droplets of herbicidal bipyridylium diquaternary salt solution dispersed in a continuous oil phase, and as a second step, agitating the first emulsion with water and a second emulsifier having a high HLB value, to give a second emulsion comprising drops of the first emulsion dispersed in a continuous aqueous phase. By low HLB value we mean a value of about 8 or less.

Preferably the continuous aqueous phase contains a solute to bring it into substantial osmotic balance with the aqueous solution of the bipyridylium diquaternary salt.

The nature of the oil used in the process of the invention is not narrowly critical and a wide variety of oils may be used. The oil may be for example a vegetable oil, for example soya bean oil, castor oil, or sunflower oil. The oil may also be a mineral oil of comparable viscosity, for example liquid paraffin.

Other oils include white oil, and the oils sold under the trade names Solvesso, Isopar, and Exsol. The Solvesso oils comprise alkylated benzenes. The Isopar oils (eg. Isopar L and Isopar M) comprise isoparaffinic hydrocarbons. The Exsol oils comprise de-aromatised paraffinic hydrocarbons. Diesel oil may also be used. Commercially available diesel oil usually contains additives to lower its freezing point and to prevent wax separation. These do not appear to affect the use of the oil in the present invention. The gas oil from which commercial diesel oil is prepared is also suitable for use in the process of the present invention. Mixtures of oils may be used, for example mixtures of Isopar M with diesel oil in the ratio of from 1:10 to 10:1.

The expession HLB used above is an abbreviation for the term hydrophilic-lipophilic balance. HLB may be defined in terms of a numerical scale, running from 3 to 18 as described by Griffin, J. Soc. Cosmet. Chem 1, 34 (1949) and 5, 249 (1954).

Examples of emulsifiers that can be used as the first emulsifier in the process of the invention include an ABA block co-polymer of poly-12-hydroxystearic acid and polyethylene oxide. Such co-polymers are described in, for example, published U.K. Patent Application No. 2002400. A co-polymer of this kind having a molecular weight of about 5000 is referred to in the Example below as Surfactant D.

Another example of an emulsifier is a reaction product of polyisobutylenesuccinic anhydride (PIDSA) and ethanolamine, having the general formula below:

$$CH_3 - \left[ \begin{array}{c} CH_3 \\ | \\ C-CH_2 \\ | \\ CH_3 \end{array} \right]_n - CHCONHCH_2CH_2OH \\ | \\ CH_2CO_2H$$

and an average molecular weight in the range 400–5000, for example 1200. An example of such a polymer is designated as Surfactant A in the Example below. Such polymers are described in published U.K. Patent Application No. 2156799 (see for example page 3 at lines 9–65 and Examples 2 and 3). Other polymers which may be used include those described at column 5, line 26 to column 6, line 10 of U.S. Pat. No. 4,244,816. A further example of a first emulsifier is a related polymer of the above formula which has been reacted with one mole of phosphoric acid to yield the monophosphate derivative (see Example 5 of U.K. Patent Application No. 2156799). An emulsifier of this type is referred to as Surfactant B in the Example below.

Other examples of first emulsifiers include the following:

"Span" 80 (sorbitan monooleate)
Mixture of "Span" 809 with "Tween" 20 (sorbitan monolaurate condensed with 20 molar proportions of ethylene oxide)
"Tween 85" (sorbitan trioleate condensed with 20 molar proportions of ethylene oxide)
Lecithin (phosphatidylcholine)
"Atlox" 1045A (polyoxyethylene sorbitol oleate/laurate)
"Span" 80/lecithin mixtures
"Arlacel" 83 (sorbitan sesquioleate), optionally mixed with lecithin
G 1086 (polyoxyethylene sorbitol hexa-oleate)

Particular examples of mixtures of emulsifiers include mixtures of ∓Arlacel" 83 with lecithin, and mixtures of "Arlacel" 83 together with lecithin and Surfactant D referred to above, and mixtures of "Span" and "Tween" surfactants.

Examples of second emulsifiers include the condensate of p-nonylphenol with propylene oxide and ethylene oxide having the following formula:

$$C_9H_{19}-\underset{}{\bigcirc}-\left[ CH_2CH-O \atop | \atop CH_3 \right]_x \left[ CH_2CH_2O \right]_y H$$

wherein x may be in the range from 2 to 50 or more, and y may be in the range from 10 to 100 or more.

The emulsifier referred to as Surfactant C in the Example below is a condensate of the last foregoing formula in which x has values ranging from 10 to 16 with an average value of 13.5 and y has values ranging from 28 to 38 with an average value of 33. Other members of this series having different values for y are referred to below by the code names shown in the following table.

| Values of y | Name |
| --- | --- |
| 40–50 | Surfactant E |
| 75–85 | Surfactant F |
| 170–180 | Surfactant G |

Another material useful in preparing the second emulsion is a copolymer of the product referred to above as PIBSA having a molecular weight of about 1000, which is copolymerised with methoxypolyethylene glycol in a molar ratio of 1:2. This co-polymer is referred to below as Surfactant H. A further material useful as a second emulsifier comprises a modified polyester with an HLB value of 13 to 15 sold under the code number A109.

Additional second emulsifiers include condensates of para-nonylphenol with ethylene oxide residues. The product having 20 ethylene oxide residues is referred to below as Surfactant I and the product with 35 ethylene oxide residues is referred to below as Surfactant J. Condensates of $C_{13}$ to $C_{15}$ alkanols with from 2 to 50 molar proportions of ethylene oxide may also be used as second emulsifiers. An example of this class containing 30 molar proportions of ethylene oxide is referred to below as Surfactant K. Other examples of second emulsifiers include those emulsifiers sold under the Trade Names "Pluronic" and "Tween" and polyvinyl alcohol.

The "Pluronic" emulsifiers are block copolymers of polyethylene oxide and polypropyleneoxide. Particular examples of these include the following:

| Code No. | Percentage of ethylene oxide | Molecular weight |
| --- | --- | --- |
| F38 | 80 | 4750 |
| L92 | 20 | 3438 |
| P65 | 50 | 3500 |
| F68 | 80 | 8750 |
| F88 | 80 | 11250 |
| F108 | 80 | 16250 |
| P94 | 40 | 4583 |

The "Tween" series of emulsifiers comprises a range of sorbitan esters condensed with various molar proportions of ethylene oxide. These emulsifiers may be used alone or in combination with emulsifiers of the type of, for example, Surfactant C referred to above.

Other emulsifiers that may be used include the following products produced by Rhone-Poulenc:

| Code No. | Chemical composition |
| --- | --- |
| BSU | Ethoxylated polyarylphenol |
| FL | Ethoxylated polyarylphenol phosphate neutralised with triethanolamine |
| 3033 | Phosphoric ester of ethoxylated arylphenol |
| 40884 | Sulphated polyarylphenol ethoxylate |

In order to improve the stability of the multiple emulsions prepared by the process of the invention to be stable on storage, it is preferred that the continuous aqueous phase of the second emulsion is in at least approximate osmotic balance with the aqueous solution of herbicidal bipyridylium diquaternary salt used in preparing the emulsions of the invention. This may conveniently be achieved by including in the continuous aqueous phase of the second emulsion a solute which has a molarity with respect to chloride ion similar to that of the anion in the aqueous solution of the herbicidal bipyridylium diquaternary salt. A convenient solute is sodium chloride. Thus, by way of example, an aqueous solution containing 376 grams per liter of paraquat dichloride is approximately 4.0M with respect to chloride ion. The continuous aqueous phase in the second emulsion should therefore be 4.0 molar with respect to sodium chloride; that is to say, it should contain 235.75 grams (4.0M) of sodium chloride per liter.

At higher concentrations of paraquat, dissociation into paraquat cation and chloride anions may be incomplete and the concentration of the sodium chloride in the continuous aqueous phase may need to be adjusted to compensate for the departure of the osmotic pressure of the paraquat chloride solution from the theoretical value. This means that 1- or 2-molar sodium chloride may be sufficient in the above example. Solutions other than sodium chloride solutions may be used as the continuous aqueous phase in the compositions of the invention. Thus solutions of other electrolytes (eg. potassium nitrate) or non-electrolytes (e.g. sucrose) may be employed. However sodium chloride solutions are particularly convenient since sodium chloride is cheap and readily available.

The agitation of the aqueous solution of the herbicidal bipyridylium diquaternary salt with an oil to form the first emulsion may be carried out for example by high speed stirring (using for example an Elado stirrer, which operates at speeds for example of up to 25,000 revolutions per minute).

The agitation of the first emulsion with the aqueous solution to give the second emulsion may be carried out for example by low-speed stirring using a conventional paddle stirrer at very low speeds. Alternatively, high-speed stirring may be used, but if so, it should be used only for a very short time.

Methods of agitating other than those referred to above may be used to prepare the emulsions according to the invention. Thus, the preparation of the first emulsion may be carried out by pressure homogenisation, or by use of ultra-sonic agitation. The preparation of the second emulsion may be carried out for example by use of static mixers. The period of agitation required to form the emulsions may vary according to the scale on which the emulsions are prepared, but may readily be ascertained by simple trials. Generally, in the preparation of quantities of the order of 1 to 5 liters, the preparation of the first emulsion by high-speed stirring (eg. using an Elado stirrer) takes from 2 to 10 minutes. The preparation of the second emulsion by conventional paddle stirring usually takes from 30 to 60 minutes. If the second emulsion is prepared by high-speed stirring, this may take of the order of 30 seconds.

The multiple emulsions prepared by the process of the invention may contain further ingredients to improve the retention of the herbicidal bipyridylium diquaternary salt with the drops of the first emulsion for example, thickeners for the oil phase. An example of such a thickener is polyisobutene sold, for example, under the trade name Hyvis. A wide range of polyisobutenes may be used, including those having a molecular weight of up to 100,000 or more. Other thickeners include the following:

DC 193 (a polysiloxane polymer)
Lecithin
BM 18 (polyvinyl butyral)
Bentone 34 (a sodium montmorillonite treated with an alkylammonium salt)
Aluminium stearate.

These thickeners may be incorporated at the rate of 10 to 50 grams per liter.

In addition, a coating may be induced around the drops of the first emulsion. This may be induced by including a gel-forming ingredient in the emulsions, for example sodium carboxymethyl cellulose. This material may be obtained in a range of molecular weights, for example from 44000 (grade F20P) to 200,000 (grade F 1000P). Intermediate grades include F75P (MW 80,000) and F350P (120,000). The carboxymethyl cellulose is preferably used in conjunction with a salt of a polyvalent cation (e.g. aluminium chloride or sulphate) dissolved in the continuous aqueous phase, so as to produce a coating or film on the drops of the first emulsion. The strength of the gel coating may be adjusted by addition of acid (eg. citric acid). Alternatively, the polyvallent cation may be omitted and gel strength adjusted by pH variation only. Another cation which may be used in conjunction with sodium carboxymethyl cellulose is an alkyltrimethyl-ammonium cation such as one of the alkyltrimethylammonium chlorides of formula $RN(CH_3)^+_3Cl^-$ (*where R is* $C_{10}$ to $C_{18}$) alkyl) sold under the trade name Arquad. Such a coating or film may also be produced by the addition of xanthan gum, used in conjunction with a salt of a polyvalent cation (e.g. ceric chloride) or a borate salt (e.g. sodium borate) dissolved in the continuous aqueous phase.

Other materials which may be used to produce a coating on the drops of the first emulsion include sodium polymethylmethacrylate condensed with ethylene oxide. This coating agent is used at a pH less than 7. It can also be gelled by addition of aluminium salts. Gelatine or gum arabic may also be used as coating agents at a pH of less than 7. Other coating agents include alginates and guar gum, used in conjunction with an electrolyte (eg. aluminium chloride or sulphate). The use of coating agents in multiple emulsions is described in U.S. Pat. No. 4,244,816, the description of which is incorporated herein by reference.

A further ingredient which may be included in the continuous aqueous phase of the multiple emulsions of the invention is a compound which will react with and deactivate any of the herbicidal bipyridylium diquaternary salt which may diffuse out from or otherwise escape from the drops of the first emulsion. Such an ingredient may be termed a bipyridylium scavenger. An example of such a compound is the condensate of formaldehyde with the sodium salt of naphthalene-2-sulphonic acid sold under the Trade Name Morwet D425, and having the structure below:

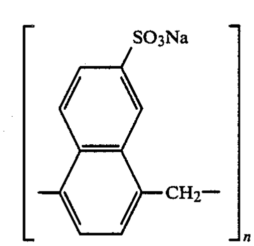

wherein n ranges from 2 to 9, with an average of 6. This material will react with, for example, paraquat dichloride to give a salt which is essentially biologically inert, both in a toxicological and a herbicidal sense.

The Morwet D425 may be included in the emulsions at a concentration of for example from 12 to 300 grams per liter of the continuous aqueous phase. Other sulphonated or sulphated compounds may also be used as bipyridylium scavengers, for example the disodium salt of chromotropic acid, having the formula:

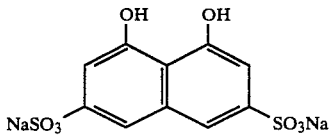

This may be included in the emulsions at a concentration of 1 to 100 grams per liter of the continuous aqueous phase. Other bipyridylium scavengers include dextran sulphate and sulphated polysaccharides generally.

Other additives whch may be included in the emulsions are Rhodopol MD50 (a polysaccharide) at a concentration of, for example, 1–10 grams per liter, alone or combined with Nalfloc (finely divided silica), at a concentration of for example from 10 to 50 grams per liter of the continuous aqueous phase.

In a modification of the process of the invention, the drops of the first emulsion may be separated from the aqueous phase by for example centrifuging the multiple emulsion. The drops of first emulsion may then be redispersed in fresh aqueous phase. This procedure may be useful if there is bipyridylium quaternary salt in the aqueous phase which was not entrapped in the oil during the preparation of the multiple emulsion.

Herbicidal bipyridylium quaternary salts which may be used as the active ingredients of the compositions of the invention include those of the following formulae:

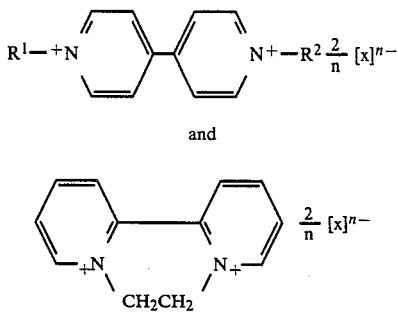

and wherein $R^1$ and $R^2$, which may be the same or different, each stand for an alkyl or alkenyl radical of 1 to 4 carbon atoms, which may be substituted by a hydroxy, carboxy, alkoxy, alkylcarbonyl, alkoxycarbonyl, carbamoyl, of N-alkyl-substituted carbamoyl radical, or a halogen atom; $[X]^{n-}$ represents an anion and n is 1, 2, 3 or 4. Preferred alkoxy groups are those containing 1 to 4 carbon atoms. Preferred alkylcarbonyl and alkoxycarbonyl groups are those containing from 2 to 5 carbon atoms. Preferred N-alkyl substituted carbamoyl radicals are those in which the N-alkyl substituent or substituents contain from 1 to 4 carbon atoms.

Examples of herbicidal bipyridylium diquaternary salts include those listed below:

1,1'-ethylene-2,2'-bipyridylium dibromide (diquat dibromide)

1,1'-dimethyl-4,4'-bipyridylium dichloride (paraquat dichloride)
1,1'-dimethyl-4,4'-bipyridylium di(methylsulphate)
1,1'-di-2-hydroxyethyl-4,4'-bipyridylium dichloride
1,1'-bis-3,5-dimethylmorpholinocarbonylmethyl-4,4'-bipyridylium dichloride (morfamquat dichloride)
1-(2-hydroxyethyl)-1'-methyl-4,4'-bipyridylium dichloride
1,1'-di-carbamoylmethyl-4,4'-bipyridylium dichloride
1,1'-bis-N,N-dimethylcarbamoylmethyl-4,4'-bipyridylium dichloride
1,1'-bis-N,N-diethylcarbamoylmethyl-4,4'-bipyridylium dichloride
1,1'-di-(piperidinocarbonylmethyl)-4,4'-bipyridylium dichloride
1,1'-diacetonyl-4,4'-bipyridylium dichloride
1,1'-diethoxycarbonylmethyl-4,4'-bipyridylium dibromide
1,1'-diallyl-4,4'-bipyridylium dibromide The names in brackets alongside some of the compounds in the above list are the accepted common names for the cationic portion of the compounds. Thus [paraquat] is the common name for the 1,1'-dimethyl-4,4'-bipyridylium cation. Paraquat is a particularly preferred bipyridylium compound for use in the compositions of the invention.

Since the herbicidal effect of a bipyridylium quaternary cation is independent of the nature of the associated anion, the choice of the anion is a matter of convenience, depending, for example, on cost. Preferably the anion is one which gives rise to a salt of convenient water solubility. Examples of anions, which may be mono- or poly-valent, include acetate, benzenesulphonate, benzoate, bromide, butyrate, chloride, citrate, fluorosilicate, fumarate, fluoroborate, iodide, lactate, malate, maleate, methylsulphate, nitrate, propionate, phosphate, salicylate, succinate, sulphate, thiocyanate, tartrate, and p-toluenesulphonate. The salt of the herbicidal bipyridylium cation may be formed from a number of similar anions or mixtures of different ones. A salt having any particular desired anion may be prepared either by direct synthesis from reactants which include the desired anion, or by exchanging the anion of a previously prepared salt of the preferred anion by methods well known in the art, for example by passage of a solution of the previously prepared salt through an ion-exchange resin. For reasons of convenience and economy, the chloride anion is a particularly preferred anion.

Since the characteristic herbicidal activity of a salt of a herbicidal bipyridylium quaternary cation resides in the cation only, it is customary to quote concentrations of active ingredients and rates of application in terms of the amount of bipyridylium quaternary cation used. Application rates and concentrations quoted in this specification therefore relate to the amount of bipyridylium quaternary cation unless otherwise stated.

In another aspect the invention further provides herbicidal compositions prepared by the process of the invention described above. The concentration of bipyridylium diquaternary cation in the compositions of the invention is preferably at least 75 grams per liter of the composition and more preferably at least 100 grams per liter. Compositions containing 200 grams or more per liter, for example 300 grams per liter, may be prepared. Especially high concentrations may be prepared by using super-saturated solutions of bipyridylium salts. Thus, hot saturated solutions of bipyridylium herbicides may be used in preparing the emulsions. As the emulsion cools, the bipyridylium herbicide solution becomes super-saturated.

Examples of compositions according to the invention include those in which the bipyridylium quaternary salt is paraquat dichloride and those in which the bipyridylium quaternary salt comprises a mixture of equal amounts of paraquat dichloride and diquat dibromide (calculated on bipyridylium cation basis).

The amount of the first emulsifier may be for example from 10 to 100 grams per liter, preferably 40 to 75 grams per liter of the first emulsion. The amount of the second emulsifier may be from 5 to 100 grams per liter, preferably 10 to 50 grams per liter of the continuous aqueous phase.

It will be evident that a composition containing a particular concentration of bipyridylium diquaternary salt may be prepared in different ways, by using different concentrations of aqueous bipyridylium salt solution in combination with different amounts of oil. In the Examples, the proportions of ingredients have been quoted in terms of volume fractions F1 and F2 where F1 is the ratio of the volume of bipyridylium diquaternary salt solution to the total volume of the first emulsion, and F2 is the ratio of the volume of first emulsion to the total volume of the finished formulation. The compositions of the invention may also comprise ingredients which have previously been proposed to reduce the hazards associated with the possibility of accidental swallowing of herbicidal bipyridylium diquaternary salts. Thus for example the compositions may contain an emetic, for example an emetic of the class disclosed in U.K. Pat. No. 1507407. A preferred emetic of this class is 2-amino-6-methyl-5-oxo-4-1-propyl-4,5-dihydro-s-triazolo[1,5-a]-pyrimidine which may be incorporated in the composition in the proportion of for example from 0.25 to 2.0 parts by weight per 100 parts of herbicidal bipyridylium diquaternary cation. The composition may also contain a colouring agent, for example a blue pigment (eg. the pigment sold under the trade name Monastral Blue). The compositions may also contain an odourant as a warning. Examples of odourants include pyridine base (see U.K. Pat. No. 1406881), valeric acid, and tetrahydrothiophene. Pyridine base may be included at a concentrated of, for example, 5 to 20 grams per liter of the composition.

An assessment of the effectiveness with which the bipyridylium diquaternary salt is retained within the drops of the emulsion may be gained by physical techniques. Thus, dialysis of a sample of the composition followed by analysis of the dialysate gives a value for the amount of bipyridylium diquaternary salt which has leaked out of the drops during the period of dialysis, plus the amount of the bipyridylium diquaternary salt which was not entrapped in the drops during the preparation of the composition. By centrifuging a sample of the composition, the continuous aqueous phase may be separated from the drops containing the dispersed droplets of aqueous bipyridylium diquaternary salt solution. Analysis of the separated continuous aqueous phase then gives a value for the amount of bipyridylium diquaternary salt which escaped entrapment in the drops during the preparation of the composition. Subtraction of this value from the value obtained from the dialysis procedure gives the amount of bipyridylium diquaternary salt which leaked out from the drops during the period of dialysis (24 hours). The amount of bipyridylium diquaternary salt which was found to have leaked out of the drops during the dialysis period ranged from 0.16% in the case of composition no 3 in Table I to 16.1% in the case of composition no 5, these percentages being based on the amount of bipyridylium salt originally present in the drops. Even at the higher value, more than 80% of the bipyridylium salt was retained within the drops. Applying the results of this in vitro test to the case where a quantity of the composition had been accidentally swallowed, this would mean that even in the least effective composition, less than 20% of the ingested bipyridylium quaternary salt would be available for absorption through the gastro-intestinal tract, an effective reduction of more than 80% in the amount of material potentially available to exert deleterious effects.

In laboratory tests with compositions according to the invention containing paraquat as the bipyridylium herbicide, there was at least a two-fold reduction in oral toxicity to rats as compared with an aqueous formulation of paraquat. In dogs, a reduction in oral toxicity of up to six-fold was observed.

The following Examples illustrate the preparation of multiple emulsions by the process of the invention.

EXAMPLE 1

The procedure followed for preparing the multiple emulsions was as follows.

The first emulsifier was dissolved in the oil with heating, and the solution allowed to cool. The amount of emulsifier used was from 50 to 100 grams per liter of the oil. A solution of paraquat dichloride in water (300 grams per liter) was added gradually to the oil/emulsifier over a period of about two minutes, with stirring by an Elado stirrer at setting 4 (on a 1–10 scale). The stirring speed was then increased to setting 6 to 7 for 10 minutes. In the resulting emulsion, the water phase occupied 65% of the volume of the emulsion.

This first emulsion was diluted with oil (30% of the volume of the emulsion) and then added slowly with stirring to a solution of sodium chloride in water (1.61 Molar) containing Surfactant C (from 5 to 15 grams per liter). Stirring was by an ordinary paddle stirrer and was continued for one hour. In an alternative procedure, the first emulsion after dilution with oil, was added quickly to the sodium chloride solution and stirred for 30 seconds only with an Elado stirrer at a low speed setting (ca 2.6). The final multiple emulsion obtained by either of these two procedures contained 50% by volume of the first emulsion diluted with oil.

The above procedure was carried out using the combinations of emulsifiers and oils shown in Table I below.

TABLE I

| Composition No | First Emulsifier & concentration in first emulsion | Oil | Concentration of second emulsifier (Surfactant C) in aqueous phase | Type of stirring in secondary emulsification |
|---|---|---|---|---|
| 1 | Surfactant A at 50 g/liter | Isopar M | 10 g/liter | Paddle stirring |
| 2 | Surfactant A | Isopar M | 10 g/liter | Paddle |

TABLE I-continued

| Composition No | First Emulsifier & concentration in first emulsion | Oil | Concentration of second emulsifier (Surfactant C) in aqueous phase | Type of stirring in secondary emulsification |
| --- | --- | --- | --- | --- |
| 3 | Surfactant A/ Surfactant D 1:1 mixture at 50 g/liter | Isopar M | 5 g/liter | stirring Paddle stirring |
| 4 | Surfactant B/ Surfactant D 7:3 mixture at 50 g/liter | Isopar M | 10 g/liter | Elado stirring for 30 seconds |
| 5 | Surfactant D at 50 g/liter | Isopar M | 10 g/liter | Paddle stirring |
| 6 | Surfactant D at 50 g/liter | Soyabean oil | 10 g/liter | Paddle stirring |

By repeating the preparation of the above compositions 1 to 6 using an aqueous solution of paraquat dichloride containing 376 instead of 300 grams of paraquat per liter, and a 2-molar solution of sodium chloride in place of the 1.61 molar solution, a series of compositions corresponding to those of Table 1 was obtained, in which the first emulsion contained 245 grams per liter of paraquat and the final multiple emulsion contained 94 grams per liter of paraquat, compared with 195 grams per liter and 75 grams per liter respectively for the compositions prepared as above.

EXAMPLE 2

This Example illustrates further compositions prepared according to the invention.

Further multiple emulsion compositions were prepared following the procedure described in Example 1. In each case a solution of paraquat dichloride containing 376 grams of paraquat per liter was used as starting material. The first emulsion was diluted with further oil so as to give a paraquat concentration in the multiple emulsion composition finally obtained of 100 grams per liter. The second emulsifier used was Surfactant C in each case, at a concentration of 10 grams per liter throughout. In each case, the secondary emulsification was carried out by paddle stirring. The compositions prepared are listed in Table 2 below:

TABLE 2

| Composition No. | First emulsifier and concentration in first emulsion | Oil |
| --- | --- | --- |
| 7 | Surfactant D 50 g/liter | White oil |
| 8 | Surfactant D 50 g/liter | Diesel oil |
| 9 | Surfactant D 50 g/liter | Isopar M and liquid paraffin 1:1 mixture |
| 10 | Surfactant B 50 g/liter | White oil |
| 11 | Surfactant B 50 g/liter | Diesel oil |
| 12 | Surfactant B 50 g/liter | Liquid paraffin |
| 13 | Surfactant A 50 g/liter | Isopar M and liquid paraffin 3:7 mixture |
| 14 | Surfactant D 50 g/liter | Isopar M and diesel oil 1:1 mixture |
| 15 | Surfactant D 50 g/liter | Isopar M and Solvesso 100 95:5 mixture |

EXAMPLE 3

This Example illustrates further compositions prepared according to the invention. The procedure described in Example 1 was followed, except that the first emulsion was not diluted by adding oil. The proportions of the ingredients used were selected to give a concentration of paraquat in the final multiple emulsion composition of 100 grams per liter. Secondary emulsification was by paddle stirring in each case. The proportions in which the oil and aqueous phases are mixed is given by the volume fractions $F_1$ and $F_2$. Thus a value of $F_1$ of 0.65 means that the paraquat solution was mixed with oil to form the first emulsion in the ratio of 0.65 parts by volume of aqueous solution to 0.35 parts of oil while a value of 0.43 for $F_2$ means that 0.43 parts by volume of the first emulsion was mixed with 0.57 parts of the continuous aqueous phase to form the final multiple emulsion composition. The compositions prepared are listed in Table 3 below.

TABLE 3

| Composition No. | First emulsifier and concentration in first emulsion in grams per liter | Oil | Electrolyte and concentration. Second emulsifier and concentration (grams per liter) in aqueous phase | Paraquat concentration g/liter and volume fractions used |
|---|---|---|---|---|
| 16 | Span 80 50 g/l | Isopar M | NaCl 1.4 M Tween 20 5 g/l | 376 $F_1 = 0.65$ $F_2 = 0.43$ |
| 17 | Arlacel 83: lecithin 7:3 mixture 50 g/l | Isopar M | NaCl 1.4 M 10 g/l Tween 20 10 g/l Surfactant C | 376 $F_1 = 0.65$ $F_2 = 0.43$ |
| 18 | Arlacel 83: lecithin 7:3 mixture 75 g/l | Isopar M | NaCl 1.4 M 10 g/l Tween 20 10 g/l Surfactant C | 376 $F_1 = 0.65$ $F_2 = 0.43$ |
| 19 | Arlacel 83: lecithin 7:3 mixture 100 g/l | Isopar M | NaCl 1.4M 10 g/l Tween 20 10 g/l Surfactant C | 376 $F_1 = 0.65$ $F_2 = 0.43$ |
| 20 | Arlacel 83: lecithin mixture 7:3 50 g/l | Isopar M | NaCl 2M surfactant C 10 g/l | 376 $F_1 = 0.53$ $F_2 = 0.5$ |
| 21 | Arlacel 83: lecithin mixture 7:3 50 g/l | Isopar M | NaCl 1.4M Tween 10 g/l G1086 5 g/l | 220 $F_1 = 0.65$ $F_2 = 0.7$ |
| 22 | Arlacel 83: lecithin mixture 7:3 50 g/l | Isopar M: diesel 1:1 mixture | NaCl 1.4M Surfactant C 10 g/l | 220 $F_1 = 0.65$ $F_2 = 0.7$ |
| 23 | Arlacel 83: licithin mixture 7.3 50 g/l | Isopar M | NaCl 2M Surfactant C 10 g/l | 376 $F_1 = 0.53$ $F_2 = 0.5$ |
| 24 | Span 20: Tween 20 mixture in 9:1 ratio 50 g/l | Isopar M | NaCl 1M Span 20 1 g/l Tween 20 9g/l | 376 $F_1 = 0.65$ $F_2 = 0.43$ |
| 25 | Span 80: Tween 20 mixture in 9:1 ratio 50 g/l | Isopar M | NaCl 1.4M Tween 20 10 g/l G1086 2 g/l | 376 $F_1 = 0.65$ $F_2 = 0.43$ |
| 26 | Span 80: Tween 20 mixture in 9:1 ratio 50 g/l | Isopar M | Sucrose 0.5M Tween 20 10 g/l | 376 $F_1 = 0.65$ $F_2 = 0.43$ |
| 27 | Arlacel 83: lecithin 7:3 mixture 50 g/l | Isopar M | KNO$_3$ 1M Tween 20 10 g/l | 220 $F_1 = 0.65$ $F_2 = 0.7$ |
| 28 | Arlacel 83 32 g/l Lecithin 15 g/l Surfactant D 3g/l | Isopar M | NaCl 1M Surfactant C 10 g/l | 220 $F_1 = 0.65$ $F_2 = 0.7$ |

EXAMPLE 4

This Example illustrates further compositions prepared according to the invention. The procedure was as described in Example 3. The compositions prepared are listed in Table 4 below.

TABLE 4

| Composition No. | First emulsifier and concentration in first emulsion in grams per liter | Oil | Electrolyte and concentration. Second emulsifier and concentration (grams/liter) in aqueous phase | Paraquat concentration and volume fractions used |
|---|---|---|---|---|
| 29 | Surfactant D 50 g/l | Diesel | NaCl 2 M Surfactant C 10 g/l Tween 20 10 g/l | 376 $F_1 = 0.65$ $F_2 = 0.5$ |
| 30 | Surfactant D 50 g/l | Diesel | NaCl 2 M Surfactant C 10 g/l Tween 20 50 g/l | 376 $F_1 = 0.65$ $F_2 = 0.5$ |
| 31 | Surfactant D 50 g/l | Diesel | NaCl 2 M Surfactant E 10 g/l | 376 $F_1 = 0.65$ $F_2 = 0.5$ |
| 32 | Surfactant D 50 g/l | Diesel | NaCl 2 M Surfactant F 10 g/l | 376 $F_1 = 0.65$ $F_2 = 0.5$ |
| 33 | Surfactant D 50 g/l | Diesel | NaCl 2M Surfactant G 10 g/l | 376 $F_1 = 0.65$ $F_2 = 0.5$ |

TABLE 4 -continued

| Composition No. | First emulsifier and concentration in first emulsion in grams per liter | Oil | Electrolyte and concentration. Second emulsifier and concentration (grams/liter) in aqueous phase | Paraquat concentration and volume fractions used |
|---|---|---|---|---|
| 34 | Surfactant D 50 g/l | Diesel | NaCl 2M<br>Surfactant E 10 g/l<br>Tween 20 50 g/l | 376<br>$F_1 = 0.65$<br>$F_2 = 0.5$ |
| 35 | Surfactant D 50 g/l | Diesel | NaCl 2M<br>Surfactant F 10 g/l<br>Tween 20 50 g/l | 376<br>$F_1 = 0.65$<br>$F_2 = 0.5$ |
| 36 | Surfactant D 50 g/l | Diesel | NaCl 2M<br>Surfactant C 20g/l<br>Tween 20 50 g/l | 376<br>$F_1 = 0.65$<br>$F_2 = 0.5$ |
| 37 | Surfactant A 50 g/l | Isopar M | NaCl 1M<br>A109 100 g/l | 220<br>$F_1 = 0.65$<br>$F_2 = 0.7$ |
| 38 | Surfactant A 50 g/l | Isopar M | NaCl 1M<br>A109 10 g/l | 220<br>$F_1 = 0.65$<br>$F_2 = 0.7$ |
| 39 | Surfactant A 50 g/l | White oil | NaCl 1M<br>Surfactant H 10 g/l | 376<br>$F_1 = 0.65$<br>$F_2 = 0.5$ |
| 40 | Surfactant D 50 g/l | Diesel oil: Isopar M 1:1 mixture | NaCl 2M<br>Surfactant F 10 g/l | 376<br>$F_1 = 0.65$<br>$F_2 = 0.5$ |
| 41 | Surfactant D 50 g/l | Diesel oil | NaCl 2M<br>Pluronic F108 10 g/l | 376<br>$F_1 = 0.65$<br>$F_2 = 0.5$ |
| 42 | Surfactant D 50 g/l | Diesel oil | NaCl 2M<br>Surfactant C 5 g/l<br>Surfactant I 5 g/l | 376<br>$F_1 = 0.53$<br>$F_2 = 0.5$ |
| 43 | Surfactant D 50 g/l | Diesel oil | NaCl 2M<br>Surfactant C 5 g/l<br>Surfactant K 5 g/l | 376<br>$F_1 = 0.53$<br>$F_2 = 0.5$ |
| 44 | Surfactant D 50 g/l | Diesel oil | NaCl 2M<br>Surfactant J 20g/l | 376<br>$F_1 = 0.53$<br>$F_2 = 0.5$ |
| 45 | Surfactant D 50 g/l | Diesel oil | NaCl 2M<br>Surfactant J 20g/l<br>Surfactant C 10 g/l | 376<br>$F_1 = 0.53$<br>$F_2 = 0.5$ |
| 46 | Surfactant D 50 g/l | Diesel oil | NaCl 2M<br>Surfactant K 30g/l | 376<br>$F_1 = 0.53$<br>$F_2 = 0.5$ |
| 47 | Surfactant D 50 g/l | Diesel oil | NaCl 2M<br>Surfactant J 40g/l | 376<br>$F_1 = 0.53$<br>$F_2 = 0.5$ |
| 48 | Surfactant D 50 g/l | Diesel oil | NaCl 2M<br>Surfactant I 20g/l | 376<br>$F_1 = 0.53$<br>$F_2 = 0.5$ |
| 49 | Surfactant D 50 g/l | Diesel oil | NaCl 2M<br>Surfactant I 20g/l<br>Surfactant C 5 g/l | 376<br>$F_1 = 0.53$<br>$F_2 = 0.5$ |
| 50 | Surfactant D 50 g/l | Diesel oil | NaCl 2M<br>Surfactant I 5 g/l<br>Surfactant C 5 g/l | 376<br>$F_1 = 0.53$<br>$F_2 = 0.5$ |
| 51 | Surfactant D 50 g/l | Diesel oil | NaCl 2M<br>Surfactant C 10 g/l | 376<br>$F_1 = 0.53$<br>$F_2 = 0.5$ |

EXAMPLE 5

This Example illustrates further compositions prepared according to the invention containing further ingredients to improve the retention of the herbicidal bipyridylium diquaternary salt within the drops of the first emulsion. The compositions were prepared according to the procedure described in Example 3. The further ingredient(s) may be added to the aqueous solution of the bipyridylium salt or in the oil before the emulsifying process is begun. In the examples of compositions listed in Table 5 below, the bipyridylium quaternary salt used is paraquat dichloride throughout, and the concentration used was 376 grams per liter in the solution used to make the first emulsion. The volume fractions $F_1$ and $F_2$ were 0.65 and 0.50 respectively throughout, and the concentration of sodium chloride in the continuous aqueous phase was 2M except where indicated in the Table. The abbreviation CMC stands for carboxymethyl cellulose. Aluminium ion was added as aluminium sulphate hexahydrate. In some cases citric acid was added and the molar ratio of acid to aluminium ion is given in the Table.

TABLE 5

| Composition No. | First emulsifier (grams/liter) | Oil | Additive (grams/liter) | Second emulsifier (grams/liter) |
|---|---|---|---|---|
| 52 | Surfactant A 50 g/l | Isopar M | CMC F20P 10 g/l<br>CMC: $Al^{3+}$ 70:1 mole ratio<br>and citric acid:Al 6:1 mole ratio | Surfactant C 10 g/l |

TABLE 5-continued

| Composition No. | First emulsifier (grams/liter) | Oil | Additive (grams/liter) | Second emulsifier (grams/liter) |
|---|---|---|---|---|
| 53 | Surfactant A 50 g/l | Isopar M | CMC F20P 50 g/l CMC:$Al^{3+}$ mole ratio 350:1 and citric acid:$Al^{3+}$ mole ratio 6:1 | Surfactant C 10 g/l |
| 54 | Surfactant D 50 g/l | Isopar M | CMC F20P 10 g/l | Surfactant C 10 g/l |
| 55 | Surfactant D 50 g/l | Isopar M | CMC F20P 10 g/l $Al^{3+}$ 1.68g/l | Surfactant C 10 g/l |
| 56 | Surfactant D 50 g/l | Isopar M | CMC F20P 10 g/l CMC:$Al^{3+}$ ratio 70:1 Citrate:$Al^{3+}$ ratio 0.25:1 | Surfactant C 10 g/l |
| 57 | Surfactant D 50 g/l | Isopar M containing 10 g/l of Hyvis 200 | — | Surfactant C 10 g/l |
| 58 | Surfactant D 50 g/l | Isopar M containing 10 g/l of Hyvis 200 | CMC 10 g/l | Surfactant C 10 g/l |
| 59 | Surfactant D 50 g/l | soyabean oil | CMC 10 g/l | Surfactant C 10 g/l |
| 60 | Surfactant A 50 g/l | Isopar M | CMC 10 g/l pH 7 | Surfactant C 10 g/l |
| 61 | Surfactant A 50 g/l | Isopar M | CMC 20g/l pH7 | Surfactant C 10 g/l |
| 62 | Surfactant A 50 g/l | Isopar M | CMC 30g/l pH7 | Surfactant C 10 g/l |
| 63 | Surfactant A 50 g/l | Isopar M | CMC 40g/l pH7 | Surfactant C 10 g/l |
| 64 | Surfactant A 50 g/l | Isopar M | CMC 50 g/l pH7 | Surfactant C 10 g/l |
| 65 | Surfactant A 50 g/l | Isopar M | CMC F75P 5,10,30 or 50 g/l | Surfactant C 10 g/l |
| 66 | Surfactant A 50 g/l | Isopar M | CMC F35OP 5,10,30,or 50 g/l | Surfactant C 10 g/l |
| 67 | Surfactant D 50 g/l | Isopar M | CMC F75P 5 g/l with $Al^{3+}$ at molar ratio of CMC to Al of 36:1, 53:1, 91:1 and 189:1 | Surfactant C 10 g/l |
| 68* | Surfactant D 50 g/l | Diesel oil | — | Surfactant C 10 g/l |
| 69 | Surfactant D 50 g/l | Diesel oil | CMC F75P 10 g/l | Surfactant C 10 g/l |
| 70* | Surfactant D 50 g/l | Diesel oil | CMC F75P 10 g/l | Surfactant C 10 g/l |
| 71* | Surfactant D 50 g/l | Diesel oil | CMC F75P 10 g/l 1.68g/l $Al^{3+}$ | Surfactant C 10 g/l |
| 72* | Surfactant D 50 g/l | Diesel oil | CMC F75P 10 g/l | Surfactant C 10 g/l |
| 73 | Surfactant D 50 g/l | Diesel oil | CMC F75P 10 g/l CMC:$Al^{3+}$ 70:1 $Al^{3+}$:citric acid 1:0.25 | Surfactant C 10 g/l |
| 74* | Surfactant D 50 g/l | Diesel oil | CMD F75P 5 g/l Arquad ($C_{12-14}$) 0.05M | Surfactant C 10 g/l |
| 75* | Surfactant D 50 g/l | Diesel oil | CMC F75P 5 g/l Arquat ($C_{12-14}$) 0.05M | Surfactant C 10 g/l |

*Note. In compositions marked with an asterisk the concentration of sodium chloride used as the electrolyte in the continuous aqueous phase was 1M.

EXAMPLE 6

This Example illustrates further compositions prepared according to the invention. The compositions were prepared according to the procedure described in Example 3. In the examples of compositions listed in Table 6 below, the bipyridylium quaternary salt used is paraquat dichloride throughout, and is concentration was 376 grams per liter in the solution used to make the first emulsion. The volume fractions F1 and F2 were 0.65 and 0.50 respectively throughout, and the concentrations of sodium chloride in the continuous aqueous phase was 2M.

TABLE 6

| Composition No. | First emulsifier (grams/liter) | Oil | Additive (grams/liter) | Second emulsifier (grams/liter) |
|---|---|---|---|---|
| 76 | Surfactant A 25 g/l | Isopar M | — | Surfactant C 10 g/l |
| 77 | Surfactant A 50 g/l | Isopar M | — | Surfactant C 10 g/l |
| 78 | Surfactant A 75 g/l | Isopar M | — | Surfactant C 10 g/l |
| 79 | Surfactant A 100 g/l | Isopar M | — | Surfactant C 10 g/l |
| 80(a) | Surfactant A 50 g/l | Isopar M | — | Surfactant C 10 g/l |
| 81 | Surfactant A 50 g/l | Isopar M | Morwet D425 10 g/l | Surfactant C 10 g/l |
| 82 | Surfactant B 50 g/l | Isopar M | — | Surfactant C 10 g/l |
| 83 | Surfactant B 75 g/l | Isopar M | — | Surfactant C 10 g/l |
| 84 | Surfactant B 100 g/l | Isopar M | — | Surfactant C 10 g/l |
| 85 | Surfactant D 50 g/l | Soyabean oil | — | Surfactant C 10 g/l |
| 86 | Surfactant D 75 g/l | Soyabean oil | — | Surfactant C 10 g/l |
| 87 | Surfactant D 100 g/l | Soyabean oil | — | Surfactant C 10 g/l |
| 88 | Surfactant B: Surfactant D mixture in 9:1 ratio 50 g/l | Isopar M | — | Surfactant C 10 g/l |
| 89 | Surfactant B: Surfactant D mixture in 8:2 ratio 50 g/l | Isopar M | — | Surfactant C 10 g/l |
| 90 | Surfactant B: Surfactant D mixture in 7:3 ratio 50 g/l | Isopar M | — | Surfactant C 10 g/l |
| 91 | Surfactant B: Surfactant D mixture in 1:1 ratio 50 g/l | Isopar M | — | Surfactant C 10 g/l |
| 92 | Surfactant B: Surfactant D mixture in 9:1 ratio 75 g/l | Isopar M | — | Surfactant C 10 g/l |
| 93 (b) | Surfactant B: Surfactant D mixture in 8:2 ratio 75 g/l | Isopar M | — | Surfactant C 10 g/l |
| 94 (b) | Surfactant B: Surfactant D mixture in 7:3 ratio 75 g/l | Isopar M | — | Surfactant C 10 g/l |
| 95 (b) | Surfactant B: Surfactant D mixture in 1:1 ratio 75 g/l | Isopar M | — | Surfactant C 10 g/l |
| 96 | Surfactant D 50 g/l | Diesel oil | Morwet D426 24 g/l | Surfactant C 10 g/l |
| 97 (c) | Surfactant D 50 g/l | Diesel oil | Chromotropic acid (sodium salt) 10 g/l | Surfactant C 10 g/l |
| 98 (c) | Surfactant D 50 g/l | Diesel oil | Rhodopol M050 2 g/l | Surfactant C 10 g/l |
| 99 (d) | Surfactant D 50 g/l | Diesel oil | — | Surfactant C 10 g/l |

(a) Similar compositions were prepared in which the concentration of sodium chloride in the continuous aqueous phase was 0, 0.5M, 1.0M, and 1.5M.
(b) Similar compositions were also prepared containing 100 grams of the mixture of Surfactant B and Surfactant D per litre of the first emulsion.
(c) This composition was also prepared with 1-molar sodium chloride.
(d) In this Example, the concentration of paraquat in the solution used to prepare the first emulsion was 270g/litre, the volume fractions were F1 = 0.65 and F2 = 0.70, and the concentration of sodium chloride in the continuous aqueous phase was 1M.

EXAMPLE 7

This Example illustrates further compositions prepared according to the invention. The procedure used was that described in Example 3. The bipyridylium quaternary salt used was paraquat dichloride throughout, at a concentration of 376 grams per liter in the solution used to make the first emulsion. The volume fractions F1 and F2 were 0.65 and 0.50 respectively throughout, and the electrolyte was sodium chloride.

1. A concentrated herbicidal composition comprising 75 grams or more per liter of a herbicidal bipyridylium diquaternary salt of the formula:

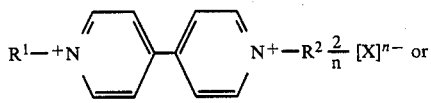

TABLE 7

| Composition No. | First emulsifier (grams/liter) | Oil | Second emulsifier (grams/liter) | Concentrations of sodium chloride |
|---|---|---|---|---|
| 100 | Surfactant D 25 g/l | Diesel oil | Surfactant F 10 g/l | 2 M |
| 101 | Surfactant D 50 g/l | Diesel oil | Surfactant C 10 g/l | 3 M |
| 102 | Surfactant D 50 g/l | Diesel oil | Surfactant F 20 g/l | 2 M |
| 103 | Surfactant D 30 g/l | Diesel oil | Surfactant C 10 g/l | 2 M |
| 104 | Surfactant D 40 g/l | Diesel oil | Surfactant C 10 g/l | 2 M |
| 105 | Surfactant D 50 g/l | Diesel oil | Surfactant C 20 g/l | 2 M |
| 106 | Surfactant D 10 g/l | Diesel oil | Surfactant C 10 g/l | 2M |
| 107 | Surfactant D 20g/l | Diesel oil | Surfactant C 10 g/l | 2M |
| 108 | Surfactant D 50 g/l | Diesel oil | Surfactant C 30 g/l | 2M |
| 109 | Surfactant D 50 g/l | Diesel oil | Surfactant C 40 g/l | 2M |
| 110 | Surfactant D 50 g/l | Diesel oil | Surfactant C 50 g/l | 2M |
| 111 | Surfactant D 50 g/l | Diesel oil | Surfactant C 75 g/l | 2M |
| 112 | Surfactant D 50 g/l | Diesel oil | Surfactant C 100 g/l | 2M |
| 113 | Surfactant D 50 g/l | Diesel oil | Surfactant C 50 g/l | 2M |

EXAMPLE 8

This Example illustrates the herbicidal activity of an emulsion according to the invention in which the herbicidal bipyridylium quaternary salt is paraquat dichloride. Appropriate quantities of the emulsion to give the application rates specified in the table below were diluted with water to a spray volume equivalent to 200 liters per hectare and sprayed on to four-week old test plants grown in a glass-house in 3-inch (ca. 7.6 cm) diameter pots. For comparison, a commercially used formulation of paraquat dichloride sold under the Trade Mark "Gramoxone" 100 comprising an aqueous solution of paraquat dichloride together with a mixture of surface-active agents was similarly diluted and applied to the test plants. Three replicates of each species of test plant were used. Seven days after application, the damage to the test plants was assessed on a scale of 0 to 10 where 0 denotes no damage and 10 complete kill, and averaged for the three replicates. The results are given in Table 8.

TABLE 8

| Treatment | Rate of application of paraquat (grams per hectare) | Test Plants | | | |
|---|---|---|---|---|---|
| | | GA | TO | AG | LL |
| "Gramoxone" | 200 | 3.3 | 6.7 | 6.7 | 8.0 |
| 100 | 300 | — | 8.3 | 8.3 | 8.7 |
| | 400 | 7.7 | 8.0 | 8.3 | 9.0 |
| | 800 | 8.0 | — | — | — |
| Composition | 200 | 3.3 | 7.7 | 6.7 | 9.0 |
| 37 | 300 | — | 8.3 | 8.3 | 9.0 |
| | 400 | 8.0 | 9.0 | 8.3 | 8.7 |
| | 800 | 8.3 | — | — | — |

The names of the test plants are as follows:
GA Galium aparine
TO Tomato (variety Ailsa Craig)
LL Lolium perenne
AG Agropyron repens

I claim:

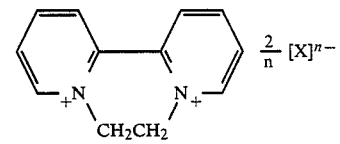

wherein R1 and R2, which may be the same or different each stand for an alkyl or alkanyl radical of 1 to 4 carbon atoms, which may be substituted by a hydroxy, carboxy, alkoxy, alkylcarbonyl, alkoxycarbonyl, carbamoyl or N-alkyl-substituted carbamoyl radical or a halogen atom; $[X]^{n-}$ represents an anion and n is 1, 2, 3 or 4; the said composition having a reduced oral toxicity towards mammals as compared with compositions consisting of a concentrated aqueous solution of a herbicidal bipyridylium diquaternary salt, the said compositions being prepared by a process comprising as a first step agitating an aqueous solution of a herbicidal bipyridylium diquaternary salt with an oil and a first emulsifier having a low HLB value to give a first emulsion comprising droplets of herbicidal bipyridylium diquaternary salt solution dispersed in a continuous oil phase, and as a second step, agitating the first emulsion with water and a second emulsifier having a high HLB value to give a second emulsion comprising drops of the first emulsion dispersed in a continuous aqueous phase, and wherein the water used to prepare the second emulsion contains a solute in sufficient concentration to bring the continuous aqueous phase into substantial osmotic balance with the aqueous solution of the herbicidal bipyridylium diquaternary salt.

2. A composition as claimed in claim 1 wherein the herbicidal bipyridylium diquaternary salt is a salt of the 1,1'-dimethyl-4,4'-bipyridylium ion.

3. A composition as claimed in claim 1 or claim 2 wherein the solute is sodium chloride.

4. A composition as claimed in any of claims 1, 3 or 23 wherein the oil comprises diesel oil or Isopar M or mixtures thereof.

5. A composition as claimed in any of claims 1, 3, 4, or 24 wherein the emulsifier of low HLB value comprises a block co-polymer of poly-12-hydroxy stearic acid and polyethylene oxide; a reaction product of polyisobutylenesuccinic anhydride and ethanolamine having the formula:

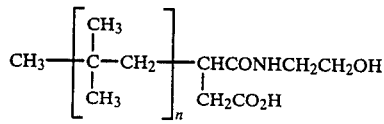

having a molecular weight in the range 400 to 5000; or a compound of the last foregoing formula reacted with a molar proportion of phosphoric acid to yield the monophosphate derivative.

6. A composition as claimed in any of claims 1, 3, 4, 5 or 25 wherein the emulsifier of high HLB value comprises a condensate of p-nonylphenol with propylene oxide and ethylene oxide and having the following formula:

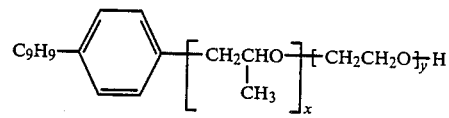

wherein x may be from 2 to 50 and y may be from 10 to 100, or sorbitan monolaurate condensed with 20 molar proportions of ethylene oxide.

7. A composition as claimed in any of claims 3, 4, 5, 6 or 26 wherein the emulsion comprises one or more further ingredients to improve the retention of the herbicidal bipyridylium diquaternary salt within the droplets dispersed in the continuous oil phase, such ingredients comprising polyisobutene; sodium carboxymethyl cellulose in conjunction with an alkyltrimethylammonium salt or a polyvalent cation; xanthan gum in conjunction with a polyvalent cation or a borate salt; gum arabic; guar gum; gelatine; or sodium polymethylmethacrylate condensed with ethylene oxide.

* * * * *

UNITED STATES PATENT AND TRADEMARK OFFICE
CERTIFICATE OF CORRECTION

PATENT NO. : 4,875,927

DATED : October 24, 1989

INVENTOR(S) : TADROS

It is certified that error appears in the above-identified patent and that said Letters Patent is hereby corrected as shown below:

Col. 21, lines 1-5, delete

"1. A concentrated herbicidal composition comprising 75 grams or more per liter of a herbicidal bipyridylium diquaternary salt of the formula:

Col. 22, line 41, insert

--1. A concentrated herbicidal composition comprising 75 grams or more per liter of a herbicidal bipyridylium diquaternary salt of the formula:

UNITED STATES PATENT AND TRADEMARK OFFICE
CERTIFICATE OF CORRECTION

PATENT NO. : 4,875,927

DATED : October 24, 1989

INVENTOR(S) : Tadros

It is certified that error appears in the above-identified patent and that said Letters Patent is hereby corrected as shown below:

Claim 4, delete "1, 3 or 2 3" and insert --1, 2 or 3--.

Claim 5, delete "1, 3, 4, or 2 4" and insert --1 to 4--.

Claim 6, delete "1, 3, 4, 5 or 2 5" and insert --1 to 5--.

Claim 7, delete "3, 4, 5, 6 or 2 6" and insert --1 to 6--.

Signed and Sealed this

Twenty-sixth Day of February, 1991

Attest:

HARRY F. MANBECK, JR.

*Attesting Officer*     *Commissioner of Patents and Trademarks*